United States Patent [19]

Nakanishi et al.

[11] 4,010,184

[45] * Mar. 1, 1977

[54] THIENODIAZEPINES

[75] Inventors: Michio Nakanishi, Nakatso; Kazuhiko Araki, Yoshitomi; Tetsuya Tahara, Yoshitomi; Masami Shiroki, Yoshitomi, all of Japan

[73] Assignee: Yoshitomi Pharmaceutical Industries, Ltd., Osaka, Japan

[*] Notice: The portion of the term of this patent subsequent to Oct. 8, 1991, has been disclaimed.

[22] Filed: Mar. 20, 1974

[21] Appl. No.: 453,117

[30] Foreign Application Priority Data

Mar. 20, 1973 Japan .............................. 48-32159
Apr. 18, 1973 Japan .............................. 48-44423

[52] U.S. Cl. ................. 260/332.2 R; 260/294.8 D; 260/332.2 A; 260/332.3 P; 260/332.5; 424/795

[51] Int. Cl.² ...................................... C07D 333/24

[58] Field of Search ............ 260/332.2 A, 239 BC, 260/239 BE, 239 BD, 332.2 R

[56] References Cited

OTHER PUBLICATIONS

Masuda "Chemical Abstracts" vol. 76 (1972) p. 46225z.
Nakanishi "Journal of Medicinal Chemistry" (1973) vol. 16, No. 3, pp. 214–219.

Primary Examiner—James O. Thomas, Jr.
Assistant Examiner—A. Siegel
Attorney, Agent, or Firm—Sughrue, Rothwell, Mion, Zinn & Macpeak

[57] ABSTRACT

Thienodiazepines of the formula:

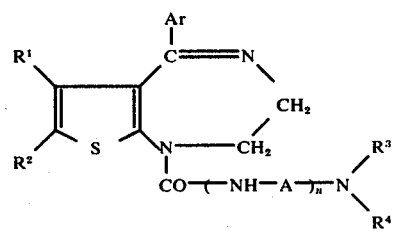

wherein Ar is mono- or di-substituted phenyl [the substituents(s) being H, halogen, $C_{1-4}$ alkyl or $C_{1-4}$ alkoxy] or pyridyl; $R^1$ is H or $C_{1-4}$ alkyl; $R^2$ is H, halogen or $C_{1-4}$ alkyl; or $R^1$ and $R^2$ combinedly form $-(CH_2)_4-$; each of $R^3$ and $R^4$ is $C_{1-4}$ alkyl, or $R^3$ and $R^4$ together with the adjacent nitrogen atom form a heterocyclic group; A is $C_{2-4}$ alkylene; and n is an integer of zero and 1; and pharmaceutically acceptable acid addition salts thereof are disclosed. They are useful as analgesics.

9 Claims, No Drawings

THIENODIAZEPINES

BACKGROUND OF THE INVENTION

A number of benzodiazepine compounds exhibit excellent depressant activity on the central nervous system (CNS) such as sedative, muscle relaxant and anticonvulsant activity, and some of the compounds are used widely as minor tranquillizers and anticonvulsants in the clinical field.

Thienodiazepine compounds are also known to exhibit excellent depressant activity on CNS as disclosed, for example, by M. Nakanishi et al. in Journal of Medicinal Chemistry, Vol. 10, No. 3, pp. 214–219 (1973).

On the contrary, thiendiozepines of the present invention exhibit remarkably different activity compared with the known diazepine compounds, namely it is found that the thienodiazepines of the present invention exhibit more potent in analgesic activity and less potent in CNS depressant activity. Analgesic activity of the known diazepine compounds is fairly weak, and that analgesic activity thereof may be attributed to a secondary induction from CNS depressant activity.

The Japanese Patent Application Publication No. 71-39349 (cf. Chemical Abstracts Vol. 76, 46225z (1972)) and U.S. Application Ser. No. 242768 now Pat. No. 3,840,558 disclose 1-dimethylcarbamoylbenzodiazepine compounds and 1-monomethylcarbamoyl-thienodiazepine compounds as having utility as minor tranquillizers and anticonvulsants.

We have disclosed a prototype of thienodiazepines having utility as analgesics.

DETAILED DESCRIPTION OF THE INVENTION

This invention relates to novel and therapeutically valuable thienodiazepines of the formula:

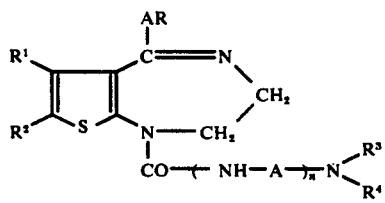

and pharmaceutically acceptable acid addition salts thereof, wherein Ar is a member selected from the group consisting of mono- or di-substituted phenyl [the substituent(s) being a member selected from the group consisting of a hydrogen atom, a halogen atom (e.g. Cl, Br or F), an alkyl group having 1 to 4 carbon atoms (e.g. methyl, ethyl, propyl, isopropyl or butyl) and an alkoxy group having 1 to 4 carbon atoms (e.g. methoxy or ethoxy)] and pyridyl; $R^1$ is a member selected from the group consisting of a hydrogen atom and an alkyl group having 1 to 4 carbon atoms (e.g. methyl, ethyl or propyl); $R^2$ is a member selected from the group consisting of a hydrogen atom, a halogen atom (e.g. Cl, Br or F) and an alkyl group having 1 to 4 carbon atoms (e.g. methyl, ethyl or propyl); or $R^1$ and $R^2$ combinedly form a tetramethylene group, i.e. $-(CH_2)_4-$; each of $R^3$ and $R^4$ is an alkyl group having 1 to 4 carbon atoms (e.g. methyl, ethyl or propyl), or $R^3$ and $R^4$ together with the adjacent nitrogen atom form a heterocyclic group [e.g. 1-pyrrolidinyl, piperidino, morpholino or 1-piperazinyl which bear an alkyl group having 1 to 4 carbon atoms (e.g. methyl or ethyl) in the 4-position]; A is a straight or branched alkylene group having 2 to 4 carbon atoms (e.g. ethylene, trimethylene, propylene, 2-methyltrimethylene or tetramethylene); and $n$ is an integer of zero and 1.

The compounds of formula [I] can be produced by reacting a compound of the formula:

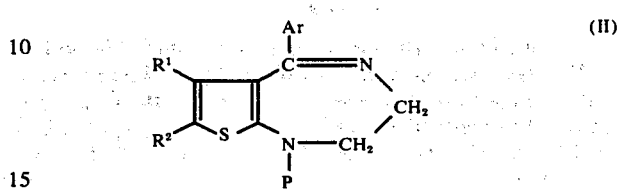

with a compound of the formula:

wherein one of P and Q is a hydrogen atom, and the other is a group of the formula: X—CO—, wherein X is a halogen atom; and other symbols are as defined above.

The reaction is usually carried out in an inert solvent such as a ketone (e.g. acetone, methyl ethyl ketone or cyclohexanone), an ester (e.g. ethyl acetate), an aromatic hydrocarbon (e.g. benzene, toluene or xylene), a halogenated hydrocarbon (e.g. chloroform, dichloromethane or dichloroethane), an ether (e.g. dioxane, tetrahydrofuran or diethyl ether), pyridine, dimethylformamide, dimethylsulfoxide or a mixture thereof at room temperature to the boiling point of the employed solvent for 30 minutes to several tens hours, advantageously in the presence of a deacidifying agent such as an inorganic base (e.g. sodium hydroxide, potassium hydroxide, sodium carbonate or potassium carbonate) or a tertiary amine (e.g. pyridine, triethylamine, collidine or N,N-dimethylaniline).

The compounds of formula [I] can be converted into the corresponding acid addition salts in a conventional manner by treating the compounds with various inorganic and organic acids, for example, hydrochloric, hydrobromic, sulfuric, phosphoric, nitric, methanesulfonic, p-toluenesulfonic, acetic, oxalic, maleic, fumaric, citric and camphorsulfonic acids, The compounds of the present invention have excellent analgesic activity but show weak CNS depressant activity as shown, for example, by following tests.

I. Test Compounds

1: 5-o-chlorophenyl-7-ethyl-1-dimethylcarbamoyl-2,3-dihydro-1H-thieno[2,3-e][1,4]diazepine hydrochloride (the compound of the invention)

2: 5-p-chlorophenyl-7-ethyl-1-dimethylcarbamoyl-2,3-dihydro-1H-thieno[2,3-e][1,4]diazepine hydrochloride (the compound of the invention)

3: 5-o-bromophenyl-7-ethyl-1-dimethylcarbamoyl-2,3-dihydro-1H-thieno[2,3-e][1,4]diazepine hydrochloride (the compound of the invention)

4: 5-o-chlorophenyl-7-ethyl-1-(2-diethylaminoethylcarbamoyl)-2,3-dihydro-1H-thieno[2,3-e][1,4]diazepine dihydrochloride monohydrate (the compound of the invention)

5: 5-o-chlorophenyl-7-ethyl-1-methyl-1,3-dihydro-2H-thieno[2,3-e][1,4]diazepin-2-one (Comparison)

6: 7-chloro-1-dimethylcarbamoyl-5-phenyl-1,2-dihydro-3H-1,4-benzodiazepine (Comparison)

7: 5-o-chlorophenyl-7-ethyl-1-methylcarbamoyl-2,3-dihydro-1H-thieno[2,3-e][1,4]diazepine (Comparison)

II. Methods

1. Analgesic Activity (Electrical Stimulation Method)

The test was performed essentially in accordance with the methods described in "Journal of the Pharmaceutical Society of Japan," vol 73, p. 212 ff. (1953) and "Folia Pharmacologica Japonica," vol. 65, p. 378 ff. (1969).

Test compound was administered intraperitoneally to groups consisting 10 male mice. The tail of the mouse was electrically stimulated for 5 seconds with interrupted direct current (25 volts, 40 msec., 1 cps.). When no squeak was observed during the electrical stimulation, analgesic effect was evaluated to be positive.

The $ED_{50}$ (50% effective dose) was determined graphically.

2. Anticonvulsant Activity

Pentylenetetrazole (150 mg/kg) was administered subcutaneously to groups consisting 6 mice 15 minutes after the intraperitoneal administration of the test compound. The number of dead mice were counted within 3 hours after the administration of pentylenetetrazole. On one hand, the %-inhibition at the dose equal to the $ED_{50}$ dose for analgesic activity was determined, and on the other, the $ED_{50}$, the dose required to suppress the lethal rate to 50%, was determined graphically.

III. Results

| Test Compound | Analgesic Activity $ED_{50}$ mg/kg | Anticonvulsant Activity Dose mg/kg (%-Inhibition) | A/B* |
|---|---|---|---|
| 1 | 40 | 40 (0%) | <0.4 |
| 2 | 40 | 40 (0%) | <0.4 |
| 3 | 30 | 30 (0%) | <0.4 |
| 4 | 28 | 28 (0%) | <0.4 |
| 5 | >200 | 200 (100%) | >400 |
| 6 | 170 | 170 (100%) | 2 – 4 |
| 7 | 200 | 200 (100%) | 2 – 4 |
| Aminopyrine (control) | 100 | | |

*A: $ED_{50}$ value for analgesic activity
*B: $ED_{50}$ value for anticonvulsant activity In view of various tests, including those mentioned above, the compounds of the invention represented by formula [I] and pharmaceutically acceptable acid addition salts thereof can be safely administered as analgesics in the form of a pharmaceutical preparation with a suitable and conventional carrier or adjuvant, administrable orally, without harm to the patients.

The pharmaceutical preparation can take any conventional form such as tablets, capsules or powders.

| | |
|---|---|
| Compound [I] | 50 mg |
| Lactose | 39 |
| Starch | 30 |
| Hydroxypropyl Cellulose | 1 |
| Talc | 5 |
| | 125 mg |

The daily dose of compound [I] or a salt thereof for human adults usually ranges from about 150 to 300 milligrams, in single or multiple dose, but it may be changed depending upon the age and/or symptoms of the patients. Thus, in the case of tablets each containing 50 milligrams of compound [I] or a salt thereof, three tablets per day are administered.

The present invention will be better understood from the following examples, but they are not to be construed as limiting the present invention.

EXAMPLE 1

To a solution of 32 g of 5-o-chlorophenyl-7-ethyl-2,3-dihydro-1H-thieno[2,3-e][1,4]diazepine in 100 ml of tetrahydrofuran is added 12.5 g of triethylamine, and then to this solution is added dropwise a solution of 13.2 g of dimethylcarbamoyl chloride in 30 ml of tetrahydrofuran with stirring. The whole mixture is stirred under reflux for 6 hours. After cooling, the reaction solution is transferred to water, and extracted with ethyl acetate. After the organic layer is washed with water and dried over anhydrous magnesium sulfate, the solvent is evaporated under reduced pressure. The residue is treated with ethanolic hydrogen chloride to give 5-o-chlorophenyl-7-ethyl-1-dimethylcarbamoyl-2,3-dihydro-1H-thieno[2,3-e][1,4]diazepine hydrochloride as yellow crystals. This product, when recrystallized from a mixture of methanol and ethyl acetate, melts at 240°–241° C with decomposition.

EXAMPLE 2

To a solution of 8.7 g of 1-chlorocarbonyl-5-o-chlorophenyl-7-ethyl-2,3-dihydro-1H-thieno[2,3-e][1,4]diazepine and 2.8 g of triethylamine in 50 ml of tetrahydrofuran is added dropwise 50 ml of 25%(W/V) tetrahydrofuran solution of dimethylamine with stirring. The whole mixture is refluxed with stirring for 2 hours, and then cooled and transferred to water. The resultant solution is extracted with ethyl acetate, washed with water and dried over anhydrous magnesium sulfate. The solvent is evaporated under reduced pressure. The residue is treated with ethanolic hydrogen chloride to give 5-o-chlorophenyl-7-ethyl-1-dimethylcarbamoyl-2,3-dihydro-1H-thieno[2,3-e][1,4]diazepine hydrochloride as yellow crystals. This product, when recrystallized from a mixture of methanol and ethyl acetate, melts at 240°–241° C with decomposition.

EXAMPLE 3

To a solution of 19.3 g of 5-o-chlorophenyl-7-ethyl-2,3-dihydro-1H-thieno[2,3-e][1,4]diazepine in 150 ml of tetrahydrofuran is added dropwise a solution of 10.8 g of 1-piperidinecarboxylic acid chloride in 30 ml of tetrahydrofuran with stirring. The whole solution is stirred under reflux for four and half hours. After cooling, the reaction mixture is transferred to water and extracted with ethyl acetate. After the extract is washed with water and dried over anhydrous magnesium sulfate, the solvent is evaporated under reduced pressure. The residue is treated with ethanolic hydrogen chloride to give 5-o-chlorophenyl-7-ethyl-1-piperidinocarbonyl-2,3-dihydro-1H-thieno[2,3-e][1,4]diazepine hydrochloride as yellow crystals. This product, when recrystallized from a mixture of methanol and ethyl acetate, melts at 237°–238° C with decomposition.

EXAMPLE 4

To a solution of 12.0 g of 1-chlorocarbonyl-5-o-chlorophenyl-7-ethyl-2,3-dihydro-1H-thieno[2,3-e][1,4]diazepine and 3.8 g of triethylamine in 50 ml of toluene is added dropwise a solution of 3.8 g of N-methylpiperazine in 10 ml of toluene with stirring. The whole solution is refluxed with stirring for 30 minutes, and then cooled. The precipitated triethylamine hydrochloride is filtered off. After the filtrate is washed with water and dried over anhydrous magnesium sulfate, the solvent is evaporated under reduced pressure. The residue is treated with ethanolic hydrogen chloride to give 5-o-chlorophenyl-7-ethyl-1-(4-methyl-1-piperazinylcarbonyl)-2,3-dihydro-1H-thieno[2,3-e][1,4]diazepine dihydrochloride 1/2-hydrate as yellow crystals. This product, when recrystallized from acetone containing water, melts at 248°–250° C with decomposition.

EXAMPLE 5

To 50 ml of 25%(W/V) tetrahydrofuran solution of dimethylamine is added 7.1 g of 1-chlorocarbonyl-7-ethyl-5-phenyl-2,3-dihydro-1H-thieno[2,3-e][1,4]diazepine hydrochloride by portions with cooling and stirring, and stirred at room temperature for 2 hours. The reaction mixture is transferred to water and extracted with ethyl acetate. The organic layer is washed with water and dried over anhydrous magnesium sulfate. The solvent is evaporated under reduced pressure, and the residue is treated with ethanolic hydrogen chloride to give 7-ethyl-1-dimethylcarbamoyl-5-phenyl-2,3-dihydro-1H-thieno[2,3-e][1,4]diazepine hydrochloric as yellow crystals, melting at 237°–238° C with decomposition.

EXAMPLE 6

To a suspension of 2.8 g of 5-(3,4-dichlorophenyl)-7-ethyl-2,3-dihydro-1H-thieno[2,3-e][1,4]diazepine in 50 ml of pyridine is added 1.3 g of dimethylcarbamoyl chloride, and stirred for 24 hours at 60° C. Then pyridine is evaporated under reduced pressure. To the residue is added acetone to crystallize. The crude crystals obtained are recrystallized from ethanol to give 1.3 g of 5-(3,4-dichlorophenyl)-7-ethyl-1-dimethylcarbamoyl-2,3-dihydro-1H-thieno[2,3-e][1,4]diazepine hydrochloride as pale yellow crystals, melting at 219°–221° C with decomposition.

EXAMPLE 7

To a solution of 9.3 g of 2-diethylaminoethylamine in 50 ml of tetrahydrofuran is added 7.8 g of 1-chlorocarbonyl-5-o-chlorophenyl-7-ethyl-2,3-dihydro-1H-thieno[2,3-e][1,4]diazepine hydrochloride by portions with cooling and stirring. After the mixture is reacted for 2 hours at room temperature, the reaction substance is poured into 200 ml of ice-cold water and extracted with ethyl acetate. The organic layer is washed with water and dried over anhydrous sodium sulfate and then the solvent is evaporated under reduced pressure. The residue is treated with ethanolic hydrogen chloride to give 5-o-chlorophenyl-7-ethyl-1-(2-diethylaminoethylcarbamoyl)-2,3-dihydro-1H-thieno[2,3-e][1,4]diazepine dihydrochloride monohydrate as yellow crystals. This product, when recrystalized from a mixture of methanol and ethyl acetate, melts at 150°–151° C with decomposition.

EXAMPLE 8

To a solution of 7.1 g of 2-dimethylaminoethylamine in 40 ml of tetrahydrofuran is added 7.8 g of 1-chlorocarbonyl-5-o-chlorophenyl-7-ethyl-2,3-dihydro-1H-thieno[2,3-e][1,4]diazepine hydrochloride by portions with cooling and stirring. After the mixture is reacted for one and half hours at room temperature, the reaction substance is poured into 200 ml of ice-cold water and extracted with ethyl acetate. The organic layer is washed with water and dried over anhydrous sodium sulfate and then the solvent is evaporated under reduced pressure. The residue is treated with ethanolic hydrogen chloride to give 5-o-chlorophenyl-7-ethyl-1-(2-dimethylaminoethylcarbamoyl)-2,3-dihydro-1H-thieno[2,3-e][1,4]diazepine dihydrochloric monohydrate as yellow crystals. This product, when recrystallized from a mixture of methanol and ethyl acetate, melts at 160°–162° C with decomposition.

EXAMPLE 9

To a solution of 9.2 g of 3-dimethylaminopropylamine in 50 ml of tetrahydrofuran is added 7.8 g of 1-chlorocarbonyl-5-o-chlorophenyl-7-ethyl-2,3-dihydro-1H-thieno[2,3-e][1,4]diazepine hydrochloride by portions with cooling and stirring. After the mixture is reacted for two and half hours at room temperature, the reaction substance is poured into 200 ml of ice-cold water and extracted with ethyl acetate. The organic layer is washed with water and dried over anhydrous sodium sulfate and then the solvent is evaporated under reduced pressure. The residue is treated with ethanolic hydrogen chloride to give 5-o-chlorophenyl-7-ethyl-1-(3-dimethylaminopropylcarbamoyl)-2,3-dihydro-1H-thieno[2,3-e][1,4]diazepine dihydrochloride as yellow crystals. This product, when recrystallized from a mixture of methanol and ethyl acetate, melts at 223°–224° C with decomposition.

EXAMPLE 10

To a solution of 5.8 g of 5-o-chlorophenyl-7-ethyl-2,3-dihydro-1H-thieno[2,3-e][1,4]diazepine in 50 ml of pyridine is added 4.5 g of 3-morpholinopropylcarbamoyl chloride and stirred for 24 hours at 60° C. Then pyridine is evaporated under reduced pressure, and to the residue is added acetone to crystallize. The crude crystals obtained are recrystallized from ethanol to give 5-o-chlorophenyl-7-ethyl-1-(3-morpholinopropylcarbamoyl)-2,3-dihydro-1H-thieno[2,3-e][1,4]diazepine dihydrochloride as yellow crystals, melting at 225°–238° C with decomposition.

EXAMPLE 11

To a solution of 5.8 g of 5-o-chlorophenyl-7-ethyl-2,3-dihydro-1H-thieno[2,3-e][1,4]diazepine in 50 ml of pyridine is added 4.2 g of 2-piperidinoethylcarbamoyl chloride, and the mixture is stirred for 24 hours at 60° C. Then pyridine is evaporated under reduced pressure, and to the residue is added acetone to crystallize. The crude crystals obtained are recrystallized from ethanol to give 5-o-chlorophenyl-7-ethyl-1-(2-piperidinoethylcarbamoyl)-2,3-dihydro-1H-thieno[2,3-e][1,4]diazepine dihydrochloride 1/2hydrate as yellow crystals, melting at 215°–216° C with decomposition.

EXAMPLE 12

To a solution of 5.5 g of 7-ethyl-5-p-fluorophenyl-2,3-dihydro-1H-thieno[2,3-e][1,4]diazepine in 50 ml of tetrahydrofuran is added 2.2 g of triethylamine, and then to this solution is added dropwise a solution of 2.4 g of dimethylcarbamoyl chloride in 10 ml of tetrahydrofuran with stirring. The whole mixture is stirred under reflux for 6 hours. After cooling, the reaction solution is transferred to water, and extracted with ethyl acetate. After the organic layer is washed with water and dried over anhydrous magnesium sulfate, the solvent is evaporated under reduced pressure. The residue is treated with ethanolic hydrogen chloride to give 7-ethyl-5-p-fluorophenyl-1-dimethylcarbamoyl-2,3-dihydro-1H-thieno[2,3-e][1,4]diazepine hydrochloride as pale yellow crystals. This product, when recrystallized from ethanol, melts at 216°–218° C with decomposition.

EXAMPLE 13

To a suspension of 5.1 g of 7-ethyl-5-(2-pyridyl)-2,3-dihydro-1H-thieno[2,3-e][1,4]diazepine in 50 ml of pyridine is added 2.4 g of dimethylcarbamoyl chloride, and stirred for 24 hours at 60° C. Then pyridine is evaporated under reduced pressure. To the residue is added acetone to crystallize. The crude crystals obtained are recrystallized from ethanol to give 7-ethyl-1-dimethylcarbamoyl-5-(2-pyridyl)-2,3-dihydro-1H-thieno[2,3-e][1,4]diazepine dihydrochloride, melting at 183°–192° C with decomposition.

Using the procedure set forth in the above examples, but substituting equivalent amounts of the appropriate starting compounds, the following compounds are also produced:

1. 5-o-chlorophenyl-7-methyl-1-dimethylcarbamoyl-2,3-dihydro-1H-thieno[2,3-e][1,4]diazepine hydrochloride, yellow crystals, melting at 238°–239° C with decomposition (from acetone containing water);
2. 5-o-chlorophenyl-7-ethyl-1-diethylcarbamoyl-2,3-dihydro-1H-thieno[2,3-e][1,4]diazepine hydrochloride, yellow crystals, melting at 224°–226° C with decomposition (from methanol-ethyl acetate);
3. 5-o-chlorophenyl-7-ethyl-1-(1-pyrrolidinylcarbonyl)-2,3-dihydro-1H-thieno[2,3-e][1,4]diazepine hydrochloride, yellow crystals, melting at 236°–237° C with decomposition (from methanol-acetone);
4. 5-o-chlorophenyl-7-ethyl-1-morpholinocarbonyl-2,3-dihydro-1H-thieno[2,3-e][1,4]diazepine hydrochloride, yellow crystals, melting at 234°–235° C with decomposition (from methanol-acetone);
5. 5-o-chlorophenyl-6,7-dimethyl-1-dimethylcarbamoyl-2,3-dihydro-1H-thieno[2,3-e][1,4]diazepine hydrochloride, yellow crystals, melting at 246° C with decomposition (from methanol-ethyl acetate);
6. 5-o-chlorophenyl-1-dimethylcarbamoyl-2,3,6,7,8,9-hexahydro-1H-[1]benzothieno[2,3-e][1,4]diazepine hydrochloride, yellow crystals, melting at 214°–215° C with decomposition (from methanol-ethyl acetate);
7. 7-ethyl-1-dimethylcarbamoyl-5-o-tolyl-2,3-dihydro-1H-thieno[2,3-e][1,4]diazepine hydrochloride, yellow crystals, melting at 225°–226° C with decomposition (from methanol-ethyl acetate);
8. 7-ethyl-5-o-methoxyphenyl-1-dimethylcarbamoyl-2,3-dihydro-1H-thieno[2,3-e][1,4]diazepine hydrochloride, yellow crystals, melting at 219°–220° C with decomposition (from methanol-ethyl acetate);
9. 5-p-chlorophenyl-7-ethyl-1-dimethylcarbamoyl-2,3-dihydro-1H-thieno[2,3-e][1,4]diazepine hydrochloride, pale yellow crystals, melting at 208°–210° C with decomposition (from ethanol);
10. 5-o-bromophenyl-7-ethyl-1-dimethylcarbamoyl-2,3-dihydro-1H-thieno[2,3-e][1,4]diazepine hydrochloride, pale yellow crystals, melting at 242°–243° C with decomposition (from ethanol);
11. 7-ethyl-1-dimethylcarbamoyl-5-p-tolyl-2,3-dihydro-1H-thieno[2,3-e][1,4]diazepine hydrochloride, pale yellow crystals, melting at 216°–218° C with decomposition (from ethanol);
12. 7-ethyl-5-p-methoxyphenyl-1-dimethylcarbamoyl-2,3-dihydro-1H-thieno[2,3-e][1,4]diazepine hydrochloride, pale yellow crystals, melting at 204°–206° C with decomposition (from ethanol);
13. 7-chloro-5-o-chlorophenyl-1-dimethylcarbamoyl-2,3-dihydro-1H-thieno[2,3-e][1,4]diazepine, white crystals, melting at 132°–133° C (from ethanol-ligroin);
14. 7-ethyl-5-(3,4-dimethoxyphenyl)-1-dimethylcarbamoyl-2,3-dihydro-1H-thieno[2,3-e][1,4]diazepine;
15. 5-(2,4-dichlorophenyl)-7-ethyl-1-dimethylcarbamoyl-2,3-dihydro-1H-thieno[2,3-e][1,4]diazepine;
16. 7-ethyl-1-dimethylcarbamoyl-5-(3-pyridyl)-2,3-dihydro-1H-thieno[2,3-e][1,4]diazepine;
17. 7-ethyl-1-dimethylcarbamoyl-5-(4-pyridyl)-2,3-dihydro-1H-thieno[2,3-e][1,4]diazepine;
18. 7-methyl-1-dimethylcarbamoyl-5-(2-pyridyl)-2,3-dihydro-1H-thieno[2,3-e][1,4]diazepine;
19. 6,7-dimethyl-1-dimethylcarbamoyl-5-(2-pyridyl)-2,3-dihydro-1H-thieno[2,3-e][1,4]diazepine.

Although the present invention has been adequately discussed in the foregoing specification and examples included therein, one readily recognizes that various changes and modifications may be made without departing from the spirit and scope thereof.

What is claimed is:
1. Thienodiazepines of the formula:

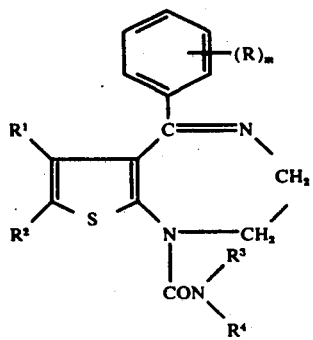

wherein R is a halogen atom; each of $R^1$ and $R^2$ is a hydrogen atom or an alkyl group having 1 to 4 carbon atoms; each of $R^3$ and $R^4$ is an alkyl group having 1 to 4 carbon atoms; and m is an integer of one or two; and pharmaceutically acceptable acid addition salts thereof.

2. The compound of claim 1:
5-o-Chlorophenyl-7-ethyl-1-dimethylcarbamoyl-2,3-dihydro-1H-thieno[2,3-e][1,4]diazepine.

3. The compound of claim 1:
5-o-Chlorophenyl-7-methyl-1-dimethylcarbamoyl-2,3-dihydro-1H-thieno[2,3-e][1,4]diazepine.

4. The compound of claim 1:
5-o-Chlorophenyl-7-ethyl-1-diethylcarbamoyl-2,3-dihydro-1H-thieno[2,3-e][1,4]-diazepine.

5. The compound of claim 1:
5-o-Chlorophenyl-6,7-dimethyl-1-dimethylcarbamoyl-2,3-dihydro-1H-thieno[2,3-e][1,4]diazepine.

6. The compound of claim 1:
5-p-Chlorophenyl-7-ethyl-1-dimethylcarbamoyl-2,3-dihydro-1H-thieno[2,3-e][1,4]diazepine.

7. The compound of claim 1:
5-o-Bromophenyl-7-ethyl-1-dimethylcarbamoyl-2,3-dihydro-1H-thieno[2,3-e][1,4]diazepine.

8. The compound of claim 1:
7-Ethyl-5-p-fluorophenyl-1-dimethylcarbamoyl-2,3-dihydro-1H-thieno[2,3-e][1,4]diazepine.

9. The compound of claim 1:
5-(3,4-Dichlorophenyl)-7-ethyl-1-dimethylcarbamoyl-2,3-dihydro-1H-thieno[2,3-e][1,4]diazepine.

* * * * *